United States Patent [19]

Graham

[11] 4,338,566
[45] Jul. 6, 1982

[54] MAGNETIC PARTICLE METHOD USING WATER SOLUBLE ADHESIVE FOR DETECTING FLAWS IN MAGNETIZABLE WORKPIECES

[75] Inventor: Bruce C. Graham, Arlington Heights, Ill.

[73] Assignee: Magnaflux Corporation, Chicago, Ill.

[21] Appl. No.: 113,328

[22] Filed: Jan. 18, 1980

[51] Int. Cl.$^3$ .................. G01R 33/12; G01N 27/84
[52] U.S. Cl. .................................. 324/216; 252/62.52
[58] Field of Search ........................... 324/214–216; 252/62.52

[56] References Cited

U.S. PATENT DOCUMENTS

| | | | |
|---|---|---|---|
| 2,267,999 | 12/1941 | Switzer | 324/215 |
| 2,936,287 | 5/1960 | Kazenas | 324/216 X |
| 3,073,212 | 1/1963 | Dunsheath et al. | 324/216 |
| 3,249,861 | 5/1966 | Pevar | 324/216 |
| 3,345,564 | 10/1967 | Makino et al. | 324/216 |
| 3,763,423 | 10/1973 | Forster | 324/216 X |
| 3,897,990 | 8/1975 | Bjerke | 324/216 X |
| 4,130,800 | 12/1978 | Fuchs | 324/216 |
| 4,172,315 | 10/1979 | Marsh | 324/216 X |

FOREIGN PATENT DOCUMENTS 54-36875  11/1979  Japan .................. 324/215

Primary Examiner—Gerard R. Strecker
Attorney, Agent, or Firm—Hill, Van Santen, Steadman, Chiara & Simpson

[57] ABSTRACT

Method and composition for detecting flaws in a magnetizable workpiece such as a steel billet in which the workpiece is first heated to a temperature of at least 140° F. (60° C.) in a hot water bath, the heated workpiece is removed from the bath and then magnetized either before or after the application of an indicating composition. In accordance with the present invention, the composition includes ferromagnetic particles, a fluorescent pigment and a water compatible adhesive. The flaws in the workpiece, particularly at seams, cause clusters of the indicating composition to remain to the magnetized piece where they are readily visible to an inspector.

6 Claims, No Drawings

MAGNETIC PARTICLE METHOD USING WATER SOLUBLE ADHESIVE FOR DETECTING FLAWS IN MAGNETIZABLE WORKPIECES

BACKGROUND OF THE INVENTION

1. Field of the Invention

This invention is in the field of non-destructive testing of magnetizable workpieces for nonhomogeneities in which an indicating composition in the form of a dispersion of ferromagnetic particles and fluorescent pigment particles is preferably sprayed onto the magnetizable workpiece which has been preheated in a hot water bath.

2. Description of the Prior Art

Steel billets which represent the last semifinished intermediate step between the ingot and the finished shape have been subjected to numerous types of non-destructive testing on a continuous basis, usually at a substantial velocity. A typical example of such testing procedures using magnetizable particles will be found described in U.S. Pat. No. 4,130,800.

Magnetic particle inspection in which magnetizable particles in the form of a suspension in a fluid or in dry form are applied to the surface of a magnetized piece have been in commercial use for many decades. In the inspection of billets, it is particularly important to locate seams which are longitudinal discontinuities that appear as light lines in the surface of the steel. Seams normally are closed tight enough so that no actual opening can be visually detected without magnetic particle inspection. Seams can result from a large number of sources, some of which are mechanical and some metallurgical. Brush seams are clusters of short seams that appear as though they had been painted or brushed onto the surface. Usually, these defects are the result of removal of metal from the steel surface by scarfing or scaling, exposing ingot blow-holes and the subsurface porosity. The brush type seams may range in depth from about 0.005 to 0.300 inch and may occur either in zones or across the entire surface of the billet.

Seams can also be caused by strings of non-metallic inclusions, or metallic inclusions which have a different permeability from the parent metal. Seams can also be caused by overfill or underfill in the rolls, or by cold shuts due to an overlapping of the metal from splashing in the mold.

Seams vary in difficulty to detect by means of magnetic particle inspection. Some seams are able to cause a very abrupt change in permeability in which case they are relatively easily located by conventional magnetic particle inspection. Other seams, particularly those which occur in alloy steels containing chromium and molybdenum, for example, are apparently much more difficult to locate.

In more recent time, use has been made of magnetic particles to which fluorescent pigments are attached. The inspection of the pieces is then facilitated by examining the same under ultraviolet or black light to locate the presence of occlusions of the magnetic particles. Prior art patents referring to this type of inspection technique include U.S. Pat. Nos. 2,267,999 and 2,936,287. These patents relate, respectively, to lacquer bonded and resin bonded fluorescent magnetic particles for use in this type of inspection process.

Steel billets are normally inspected in a continuous process in which the billet travels at relatively high velocity through a magnetizing yoke and through an applicator station where the fluorescent type magnetic particles are applied either in suspension or in dry form. Throughout the inspection process, the billet is likely to be handled roughly with the result that the occlusion of magnetic particles at seams and other flaws may be disturbed or even destroyed by such rough handling.

In conventional installations, the system includes a recirculating aqueous fluorescent magnetic particle bath. The inspection is carried out under black light in the dark by inspectors who mark the indications with large white or yellow crayons. The billet thus marked is then sent to scarfers or grinders who locate the seams and burn or grind them out at a conditioning station.

This type of technique has several disadvantages. Because the fluorescent magnetic particle suspension is constantly recirculated, it picks up a substantial amount of mill scale and returns it to the magnetic particle bath. Unless they are specifically descaled, billets always have a heavy, loose brittle coating of mill scale which is formed as the red hot billet cools in air. In units using the recirculating bath, substantial quantities of the scale get into the bath and are ground up. Since the mill scale is magnetic, it competes with the magnetic particles for flaw sites, and in addition masks the fluorescence and dims it appreciably. Studies have shown that typical baths may contain five to ten times as much ground up mill scale as the fluorescent magnetic particles.

Another problem which has been presented in the past is caused by seasonal change in temperatures. In several months of the year, the temperature of the billet is below the freezing point of water so that the recirculating baths have to be protected against freezing by adding an anti-freeze material such as ethylene glycol or by heating the tanks and all the plumbing. However, glycol solutions at temperatures below freezing are extremely viscous, thereby retarding the formation of indications and also increasing the dragout of the expensive glycol solution.

SUMMARY OF THE INVENTION

The present invention provides an improved method and composition for testing ferromagnetic objects, particularly steel billets, by means of fluorescent magnetic particles. The method consists in heating the workpiece to be tested to a temperature of at least 140° F. (60° C.) in a hot water bath, removing the heated workpiece from the hot water bath, magnetizing the thus treated workpiece, and applying an indicating composition including ferromagnetic particles and a fluorescent pigment together with a water compatible, water soluble adhesive to the workpiece. The workpiece is thereupon dried either naturally or by means of forced air currents, and then inspected for flaws. Driving off the water leaves the water soluble adhesive holding the indicating composition to the piece. The indicating composition is intended to be expendable, and is not recirculated. It is preferably applied by spraying which is considerably more efficient in the use of the material than is dry application or immersion in a bath. Furthermore, the problems of picking up substantial quantities of mill scale by continuous recirculation of the suspension are eliminated.

In a preferred form of the invention, the indicating composition contains water glass (sodium silicate) as the water compatible adhesive. In order to facilitate wetting of the steel surface, the indicating composition preferably also contains a surface active agent.

DESCRIPTION OF THE PREFERRED EMBODIMENTS

It is not unusual for a steel billet inspection system using the fluorescent magnetic particle technique to move the billet continuously through magnetizing yokes at speeds of about 120 feet per minute. Consequently, it is important that the aqueous suspension which is sprayed onto the surface of the billet be dried in a few seconds. In accordance with the present invention, the water remaining on the billet from the pretreatment is evaported relatively rapidly because of the temperature of the billet, and the adhesive remaining in the sprayed indicating composition after liberation of the water assures that the indication is fixed onto the surface of the billet for whatever processing the billet may undergo later. In the preferred form of the present invention, I use an adhesive material consisting of 30 or 34 Bé water glass. The amount added ranges from about 10% to about 35% by weight of the sprayed composition. At concentrations less than about 10%, the adhesion is not always sufficient, while at values in excess of about 35%, the spraying composition becomes quite viscous.

Particularly advantageous results are obtained in the process of the present invention through the use of a newly developed type of fluorescent magnetic particle which is described and claimed in copending Borrows application U.S. Ser. No. 904,764, filed Nov. 16, 1979. The Borrows application describes a composition for magnetic particle inspection which includes ferromagnetic core particles of a size ranging from about 25 to 150 microns (500 to 100 U.S. standard mesh) in maximum dimension, and daylight fluorescent pigment particles attached to the core. These particles can be attached to the core by encapsulation with a film-forming resin such as a polyamide resin which preferably contains a cascading opacifier. The fluorescent dye particles have a maximum dimension of at least 2 microns and may range from about 2 to 10 microns in maximum dimension. The maximum dimension of the ferromagnetic core particles is at least as great as the maximum dimension of the fluorescent pigment particles, and is preferably at least twice as great.

The cascading opacifier most frequently used is fluoranthene. This material has the property of absorbing rays in the ultraviolet region with the emission of additional visible light over and above what would be reflected if the substance were submitted to visible light radiation only.

The magnetic and fluorescent pigment particles and opacifier can be mixed in liquid suspension in a blender or colloid mill under sufficiently high shear to effect a cohesion between the various particles due to the operation of Van der Wall forces. In general, the blade of the blender or the rotor of the colloid mill are driven so as to rotate at a speed of at least 5400 and up to 7500 or even 12,000 rpm. Under the resulting shear due to high collision forces, the fluorescent pigment particles are caused to adhere directly to the larger magnetic particles.

Encapsulation can be carried out through the use of a relatively long chain linear polyamide derived from the reaction of dimerized linoleic acid with diamines or other polyamines. Such polyamide resins are dissolved in isopropanol or other water miscible volatile organic solvents. The premixed magnetic powder, fluorescent pigments, and opacifier are then added slowly to the resulting solution to form a slurry.

The concentration of suspended solids in the spraying composition may vary depending upon the average particle size of the fluorescent magnetic particles. For example, powders can be used at a concentration of about 1/20 ounce per gallon for particles of 5 micron average diameter, to 1/10 ounce for particles averaging 30 to 40 microns in diameter, and 1/5 to 1/10 ounce of very coarse particles. The variation occurs because finer particles contain many more particles per unit of weight, and weight concentrations need not be as high.

Steel billets normally have a rough hydrophobic surface and it is desirable to lower the water's surface tension to achieve fast wetting. When the fluorescent magnetic particles are used at a concentration of about 1/10 ounce per gallon, the following compositions may be used in the spraying composition:

Ethoxylated nonylphenol (Surface active agent—0.01–0.02% by weight
Dow Corning "Antifoam A"—0.004–0.007%
Borax—0.004–0.06%

The borax can be substituted in whole or in part by calcium acetate, calcium propinate, or sodium benzoate.

In operation, the billet is submerged in a tank of hot water having a temperature of at least 140° F. (60° C.) and preferably about 180° F. (81° C.). The billet is then passed through a standard magnetizing yoke of the type used in magnetic particle inspection processes. Then, the indicating composition containing the ferromagnetic core particles, fluorescent pigment, adhesive, and other additives is sprayed onto the surface of the billet. Any residual water can be removed by means of a hot air blast. The billet can then be inspected while being irradiated with ultraviolet light and normal white light for clusters of the fluorescent magnetic particles. This eliminates the necessity of marking the billet prior to scarfing or grinding.

The system of the present invention avoids problems which are presented by other magnetic particle application means currently employed in industry. For example, the billets when arriving for processing are free of ice and snow. The particle bath can be kept warm so that no anti-freeze is required during cold weather. The particle bath is sprayed expendably, and not poured onto the surface so as to be returned full of dirt, scale and grease to an increasingly contaminated reservoir. The indications normally last long enough to be used by conditioning personnel in locating seams to be removed, obviating the need for inspectors to mark their location. No toxic or volatile fixing solvents are necessary, so that no expensive solvent recovery means are required, nor are there any toxic hazards. Furthermore, liquid spray application is less wasteful than other liquid application means, and is dust free, compared to systems which apply the magnetic, fluorescent particles as a dry powder.

It will be evident that various modifications can be made to the described embodiments without departing from the scope of the present invention.

I claim as my invention:

1. The method of detecting flaws in a magnetizable workpiece which comprises:
heating said workpiece to a temperature of at least 140° F. (60° C.) in a hot water bath,
removing the heated workpiece from said hot water bath, magnetizing the thus treated workpiece, applying an indicating composition including ferromagnetic particles, a fluorescent pigment, and a water soluble adhesive to the workpiece, drying the workpiece to drive off residual water and thereby fix the indicating composition thereon at the location of flaws by means of said adhesive, and inspecting the workpiece for flaws indicated by the presence of clusters of said indicating composition.

2. The method of claim 1 in which:
said indicating composition is applied by spraying.

3. The method of claim 1 in which:
said water compatible adhesive is water glass.

4. The method of claim 1 in which:
said workpiece is a steel billet.

5. The method of claim 1 in which:
said indicating composition contains a surface active agent.

6. A method according to claim 1 in which:
said drying is accomplished by means of exposure of said workpiece to a hot air blast.

* * * * *